United States Patent [19]

Maurer et al.

[11] Patent Number: 5,405,436
[45] Date of Patent: Apr. 11, 1995

[54] PROCESS FOR THE PREPARATION OF HYDROXYAPATITE

[75] Inventors: Alexander Maurer, Mannheim; Gudrun Raab; Guenter Raab, both of Laudenbach; Reinhold Schmitt, Weinheim; Detlev Schober, Frankenthal; Richard Taenzler, Laudenbach, all of Germany

[73] Assignee: BK Ladenburg GmbH Gesellschaft für Chemische Erzeugnisses, Ladenburg, Germany

[21] Appl. No.: 126,969

[22] Filed: Sep. 27, 1993

[30] Foreign Application Priority Data

Sep. 28, 1992 [DE] Germany ............... 42 32 443.2

[51] Int. Cl.6 ................. C01B 25/32; A61K 7/16
[52] U.S. Cl. ........................... 106/35; 501/1; 423/309; 423/311; 424/602; 424/57
[58] Field of Search ............ 106/35; 423/309, 311, 423/160, 161; 424/602, 57

[56] References Cited

U.S. PATENT DOCUMENTS

| 4,274,879 | 6/1981 | Irvine ........................ 106/39.5 |
|---|---|---|
| 4,324,772 | 4/1982 | Conn et al. ................. 423/309 |
| 4,849,193 | 7/1989 | Palmer et al. .............. 423/308 |
| 4,931,272 | 6/1990 | Dany et al. ................. 424/49 |
| 5,180,564 | 1/1993 | Wahl et al. ................. 423/309 |

OTHER PUBLICATIONS

Dany, "Kosmetik Und Aerosole", pp. 305–310, (1978) no month.
Meyer, CA, B 1142-55, Gmelins Handbuch, Anorganic Chemistry, Calcium, Part B, pp. 1142–1155, (1961) no month.

Primary Examiner—Mark L. Bell
Assistant Examiner—C. Bonner
Attorney, Agent, or Firm—Foley & Lardner

[57] ABSTRACT

A process for the preparation of a hydroxyapatite, which is suitable as a tooth-cleaning substance, by precipitation from aqueous phosphoric acid and calcium hydroxide solution, in which a calcium-doped phosphoric acid solution is fed to an intensive mixer with a suspension of calcium hydroxide/oxide in a molar ratio of Ca:P=1.667 corresponding to the hydroxyapatite of and reacted there at precipitation temperatures of 60°–100° C., preferably 80°–90° C. and a pH of 4–8, preferably of 6.5–7.5. Also disclosed in a tooth-cleaning substance containing the hydroxyapatite.

16 Claims, 3 Drawing Sheets

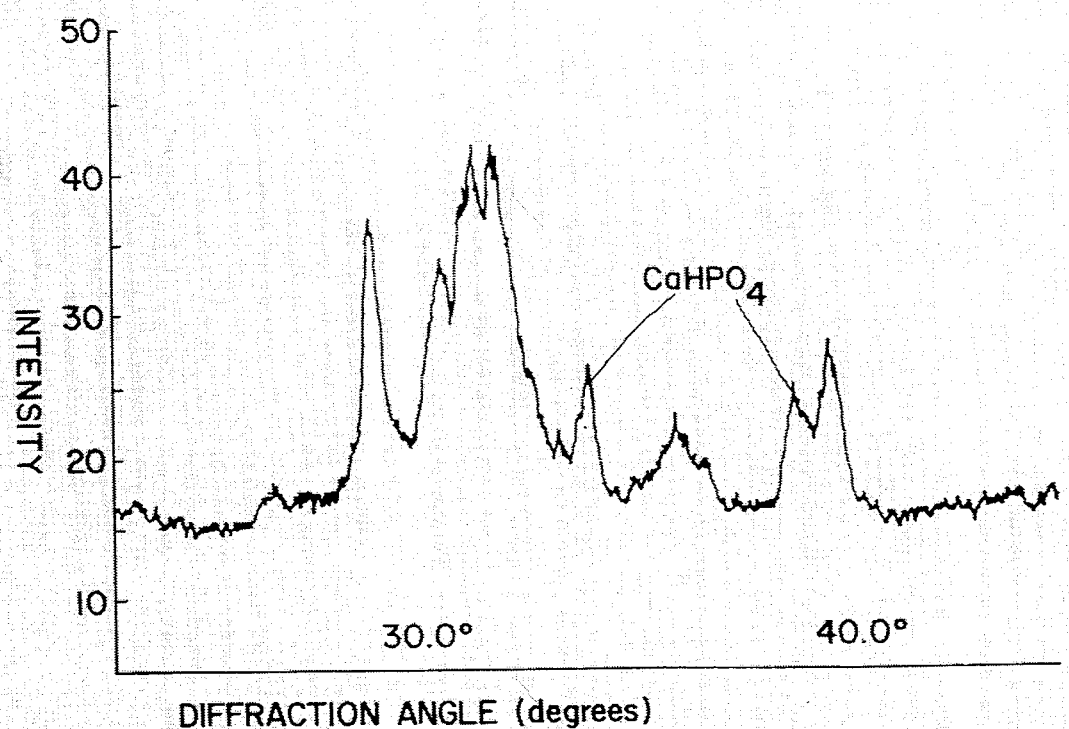

PROCESS FOR THE PREPARATION OF HYDROXYAPATITE

BACKGROUND OF THE INVENTION

The present invention relates to a novel process for the preparation of hydroxyapatite.

Many different kinds of inorganic minerals are used in oral hygiene as cleaning substances for the production of toothpastes for cleaning the teeth. To mention only a few examples, those which can be used are dicalcium phosphate, calcium carbonate, silica, Maddrell's salt, alumina and others. Of these cleaning substances, not all are noncontroversial in view of their chemical and ionic composition.

Important factors for the suitability of a material as a tooth-cleaning substance in a toothpaste are a defined hardness of the substance, a very fine and closely defined grain structure, and a specific surface constitution and/or degree of roughness and absorptiveness to water/glycerol mixtures.

The abrasiveness of tooth-cleaning substances is determined by various processes (cf. F. J. Dany: Seifen Öle, Fette, Wachse, 104 (1978), pp. 306–310). The abrasiveness of the materials according to the invention was determined by the copper plate method, but there are certain correlations between the analytical methods. To achieve a very narrow and reproducible abrasiveness, three product parameters are essential. Attention must be paid to a specific grain structure (degree of fineness), a specific surface structure on the crystal/agglomerate and a high crystallinity.

The human teeth consist largely, and in particular the outer dental enamel, of calcium phosphates or more exactly of calcium hydroxyapatite of high purity. It is therefore natural to use precipitated calcium hydroxyapatite as a cleaning substance which has a substantial identity with the natural dental enamel.

Many methods for the precipitation of hydroxyapatite are known from the literature (CA, B 1142–55). In these processes, hydroxyapatite precipitates in very finely crystalline form in nearly all solutions. The crystals tend to agglomerate in solution and during the subsequent isolation of the solid. It thus appears that only very different and hardly reproducible materials can be produced in the conventional ways by metering a calcium source—such as calcium hydroxide, milk of lime or calcium carbonate—into a dilute phosphoric acid or into a dilute alkali metal phosphate solution or conversely a phosphate/phosphoric acid solution into a milk of lime, also under closely controlled precipitation parameters from the point of view of a defined abrasiveness. It ensues from this that in all precipitation processes of industrial importance, dicalcium phosphate is coprecipitated as a by-product and cannot be removed from the final product. This material exhibits different crystal hardnesses and is therefore completely undesirable in the material according to the invention.

It is known from U.S. Pat. No. 4,274,879, for example, to prepare hydroxyapatite by mixing milk of lime with at least 60% phosphoric acid in stoichiometric amounts at temperatures of 80°–85° C. and a pH of the reaction solution of about 9.0–11.0 in a continuous reaction. The products obtained are approximately spherical crystals having a diameter of 0.03 $\mu$m to 0.5 $\mu$m and a hydroxyapatite content of 98.5–99.5%. They are suitable for preparing bone replacement parts by sintering at temperatures of 700° C. They are unsuitable as tooth-cleaning substances on account of their fineness.

It is known from U.S. Pat. No. 4,324,772 to mix, in a two-stage process, first milk of lime and phosphoric acid at 70°–85° C. and at a pH of 9.5–11, preferably at 10.5, in order to prevent formation of dicalcium phosphate impurities due to the excess of calcium hydroxide, and then to lower the pH to 7.0–7.4 in a second stage by addition of further phosphoric acid in order to neutralize excess calcium hydroxide. A hydroxyapatite having a grain size of less than 1 $\mu$m results which, if the process is not carried out exactly, contains slight impurities of included $Ca(OH)_2$. This product is unsuitable as a tooth-cleaning substance.

A further process for the preparation of hydroxyapatite is known from U.S. Pat. No. 4,849,193, in which an acidic premixture of phosphoric acid and calcium hydroxide solution is first prepared which has the approximate composition of a monocalcium phosphate and a pH of 1.5–3.5, preferably 2.0. This is slowly metered at 23° C. into a container of calcium hydroxide, a pH of over 12 being maintained, which only falls to 11–11.5 on addition of all the phosphoric acid. A finely divided hydroxyapatite is obtained which, after sintering at 1000° C., has a grain size of 0.2 $\mu$m and according to X-ray analysis is free of other calcium phosphates. This material is unsuitable as a tooth-cleaning substance.

SUMMARY OF THE INVENTION

It is therefore an object of the present invention to provide an improved process for preparing hydroxyapatite.

It is also an object of the invention to provide a process for preparing a hydroxyapatite having a relative abrasiveness according to the RDA method as described in Grabenstetter (cf. F. J. Dany: Seifen, Öle, Fette, Wachse, 104 (1978), pp. 306–310) of about 110–150.

It is a further object of the invention to provide an improved hydroxy apatite composition and improved tooth-cleaning compositions containing the hydroxyapatite formulations produced according to the process of the invention.

In accomplishing the foregoing objects, there has been provided in accordance with one aspect of the present invention a process for the preparation of a hydroxyapatite suitable as a tooth-cleaning substance, comprising the steps of simultaneously feeding an acidic calcium phosphate solution having a molar ratio of Ca:P of from about 0.2:1 to 1:1 and a calcium suspension to an intensive mixer in a substantially stoichiometric molar ratio of Ca:P to provide a reaction mixture; reacting the reaction mixture under intensive mixing at a temperature of from about 60° to about 100° C. and at a pH of from about 4 to 8 to obtain a hydroxyapatite suspension; and separating a dried hydroxyapatite from the suspension, preferably by washing the separated hydroxyapatite and drying the washed hydroxyapatite.

According to another aspect of the present invention, there has been provided a novel hydroxyapatite composition of high purity and having a narrowly-defined set of properties, as well as a tooth-cleaning composition containing this hydroxyapatite formulation.

Further objects, features and advantages of the present invention will become apparent to persons skilled in the art from the detailed description of preferred embodiments that follows, when considered together with the appended figures of drawing.

BRIEF DESCRIPTION OF THE DRAWINGS

In the drawings:

FIGS. 1a and 1b are X-ray spectrographic refraction diagrams of products prepared in Examples contained in the present application;

FIGS. 2a and 2b are scanning electron microscope photographs of products produced in Examples contained in the present application.

DETAILED DESCRIPTION OF PREFERRED EMBODIMENTS

The material prepared by the process of the invention should have a relative abrasiveness according to the RDA method of about 110–150 and additionally have a high crystallinity of a degree of crystallization of greater than about 95%, a surface area determined by BET of at most about 10 m²/g, preferably about 0.1–5 m²/g, and an average grain size of about 1–20 μm, preferably about 4–8 μm.

Figure 1B:
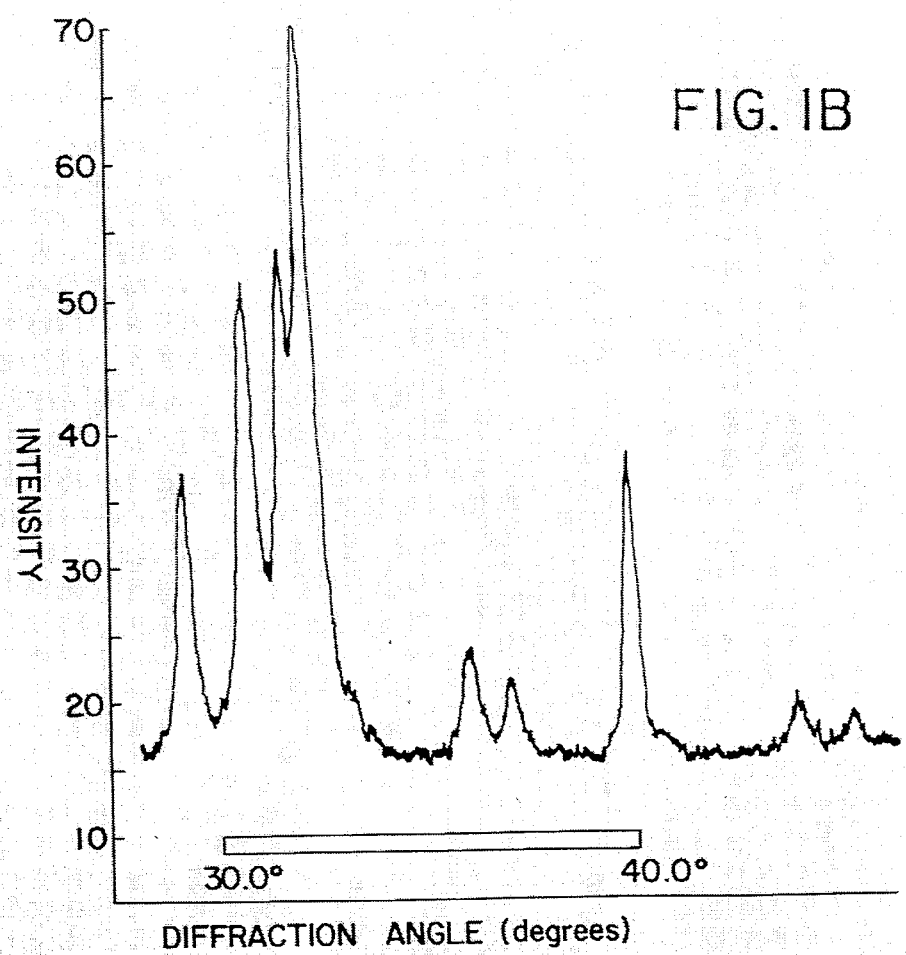
Figure 2B:

According to the process of the invention, an acidic calcium phosphate solution having a Ca:P molar ratio of about 0.2–1, preferably about 0.3–0.5, and milk of lime are combined stoichiometrically with simultaneous intensive mixing at a pH of about 4–8, preferably about 6.75–7.5, particularly preferably about 7.0–7.5, and at a temperature of about 60°–100° C., preferably about 80°–90° C. Agglomerates having fine growths which are shown in scanning electron microscope photographs (cf. FIG. 2b) are formed. These consist of a hydroxyapatite of very high crystallinity (> about 95% (cf. FIG. 1b)), and the precipitation products are free of dicalcium phosphate by-products, which is surprising since under these conditions (pH 7) dicalcium phosphate also precipitates as soon as the stoichiometric ratios correspond to this.

Figure 3:
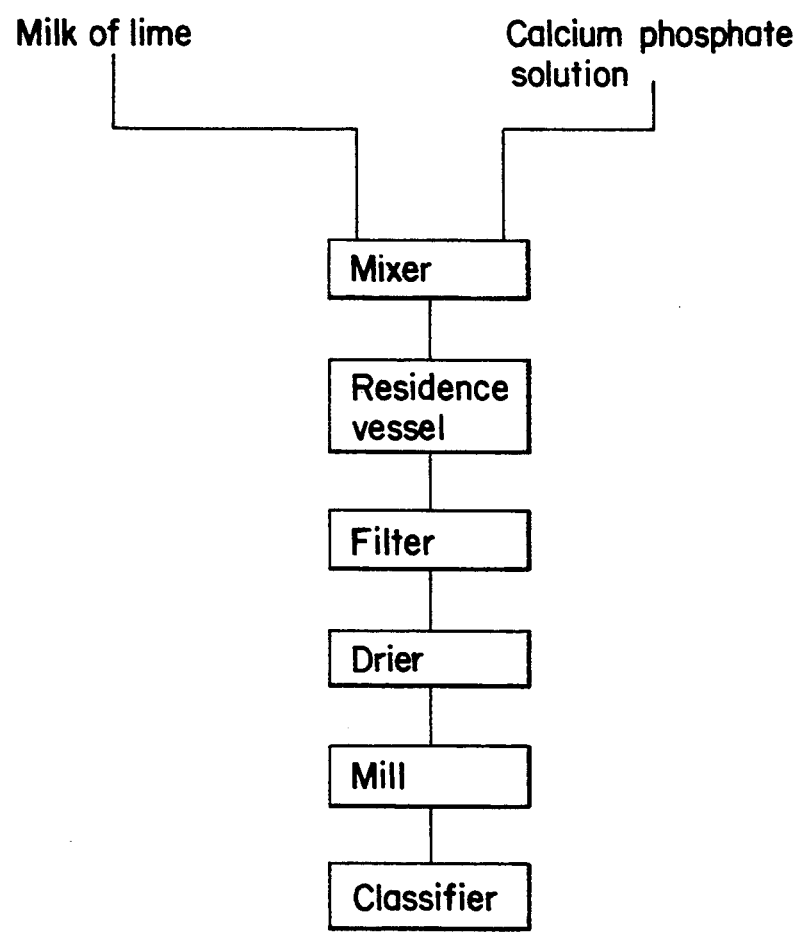
FIG. 3 is a flow diagram illustrating a preferred set of steps for carrying out the process according to the present invention.

The whole process is described in the flow diagram (FIG. 3). A calcium phosphate solution and milk of lime are passed into a continuously heated intensive mixer in a stoichiometric ratio of Ca:P = 1.667. Precipitation is carried out at temperatures between about 60° and 100° C., preferably about 80°–90° C. The pH is adjusted to about 7 and remains in a range from about 5 to 8 during stoichiometric addition of the components. The overflow from the mixer is passed into a heated stirring vessel, in which a subsequent reaction phase having an average residence time of up to about 5 hours is observed with moderate stirring and maintenance of the precipitation temperature. As a rule, about 1–2 hours' average residence time suffice; the course of the subsequent reaction is monitored by X-ray diffraction for the degree of crystallization of the final product. Suspension is continuously removed from the residence vessel and fed to a customary separator, such as e.g., a belt filter or a centrifuge, to separate off the hydroxyapatite, and is simultaneously washed there with water. The adhering water is evaporated in a drier. Subsequent grinding and drying serve to establish a narrow grain band and to destroy agglomerates arising during the drying. Particles of a size of 1–20 μm, on average 5–8 μm, are thus obtained.

The following examples of preferred embodiments are given as being merely illustrative and not limiting.

EXAMPLES

Comparison Example

By means of two differential metering balances coupled to one another, a 40% strength phosphoric acid is metered at 146.5 kg/h and a 20% strength milk of lime is metered at 380.8 kg/h (from calcium hydroxide having a Ca content of 52.3% and deionized water) into a horizontal intensive continuous mixer (effective contents 40 l), which is preheated to a temperature of 85° C. The resulting approximately 20% strength suspension, which has a pH of 7.2, is passed into a 4 m³ stirring reactor, which is kept at 90° C. A sample which was taken after 3 h, after filtering off and drying, shows on X-ray spectrographic investigation a refraction diagram (FIG. 1a) having clear dicalcium phosphate peaks and in an electron microscope photograph (FIG. 2a) a nonhomogeneous, finegrain surface. Grain size about 0.8 μm.

Example 1

A calcium-doped phosphoric acid having a Ca content of 3.0% and a $P_2O_5$ content of 28.8% is reacted at 85° C. according to the invention at a metering rate of 146.5 kg/h with a milk of lime (Ca content: 10.8%) at the rate of 328 kg/h in the apparatus described in the Comparison Example. The pH of the reaction solution here is between 7 and 8. A dicalcium phosphate-free hydroxyapatite of high crystallinity according to the refraction diagram (FIG. 1b) and of a homogeneous surface structure (FIG. 2b) results.

Example 2

26 kg of a solution having a content of 16.3% $P_2O_5$ and 3.1% Ca (prepared from lime and phosphoric acid) and 23.4 kg of a 25% strength milk of lime are fed into a water sample of 5 l by means of metering pumps in the course of 90 min into a 50 l turbulent mixing reactor preheated to 90° C. The mixture has a pH of 6.8. After a subsequent reaction time of 1 h, the slurry is concentrated in the mixer to a dry content of 80% under vacuum evaporation. The product is then dried to a moisture content of <2% in a discontinuous fluidized bed and subsequently ground in a pinned-disk mill. A hydroxyapatite according to Example 1 having the following properties is obtained:

Bulk density 900 g/l
Average grain size 6 μm
Abrasiveness 150 (copper plate test)

Example 3

The following product streams in the weight ratio 1:1.4 and a total mass flow of 900 kg/h are metered continuously by means of a differential balance system:

Component 1

Calcium phosphate solution containing 24% $P_2O_5$ and 3.5% Ca

Component 2

25% strength milk of lime from CaO and water.

The precipitation apparatus used is a 1000 l discontinuous turbulent mixing reactor with steam heating. The suspension, which has a pH of 6.5–7.8, is continuously pumped into a heated 4 m³ stirring vessel through a nozzle at ⅔ of the tank height. A flow of 750 l/h is added continuously from this to a belt filter from a degree of filling of 80%. The filter-moist cake is dried in a pneumatic-conveyor drier and ground in a classifier mill to the desired grain size of 4–10 μm.

Example 4

The procedure is carried out as in Example 3, only using a 1 m$^3$ stirring reactor having two trapezoidal stirring elements arranged on a stirrer shaft as a reactor for the reaction and a total mass flow of 700-kg/h. The preparation of the calcium monophosphate solution is carried out from calcium phosphate waste and phosphoric acid and with subsequent clarifying filtration.

What is claimed is:

1. A process for the preparation of a hydroxyapatite suitable as a tooth-cleaning substance, comprising the steps of
   simultaneously feeding an acidic calcium phosphate solution having a molar ratio of Ca:P of from about 0.2:1 to 1:1 and a calcium suspension to an intensive mixer in a substantially stoichiometric molar ratio of Ca:P to provide a reaction mixture;
   reacting the reaction mixture under intensive mixing at a temperature of from about 60° to about 100° C. and at a pH of from about 4 to 8 to obtain a hydroxyapatite suspension; and
   separating a hydroxyapatite product from the suspension.

2. A process according to claim 1, wherein said separating step includes washing the separated hydroxyapatite; and drying the washed hydroxyapatite.

3. A process according to claim 1, wherein the calcium phosphate solution comprises a solution containing a concentration of calcium phosphate of from about 20 to 50% by weight.

4. A process according to claim 1, wherein the calcium suspension comprises a calcium hydroxide suspension having a concentration of calcium hydroxide of from about 5 to 30% by weight.

5. A process according to claim 1, wherein said reacting step comprises the additional step of transferring the hydroxyapatite suspension to a separate vessel and permitting said suspension to continue reacting in said separate vessel under stirring conditions at a temperature between about 60° and 90° C. for a period of time of up to about 5 hours.

6. A process according to claim 1, wherein said pH is between about 6.75 and 7.5, and said temperature is between about 80° and 90 ° C.

7. A process according to claim 6, wherein said pH is between about 7 and 7.5.

8. A process according to claim 5, wherein said continued reaction time is between about 1 and 2 hours.

9. A process according to claim 5, wherein said continued reaction is monitored by X-ray diffraction for selection of final degree of crystallization of the hydroxyapatite product.

10. A process according to claim 1, further comprising the step of grinding the hydroxyapatite product.

11. A hydroxyapatite composition produced according to claim 1 and having a relative abrasiveness according to the RDA method of between about 110–150, a high crystallinity of a degree of crystallization of greater than about 95 %, a surface area determined by BET of at most about 10 m$^2$/g, and an average grain size of between about 1–20 μm, and wherein said hydroxyapatite composition contains substantially no dicalcium phosphate.

12. A hydroxyapatite composition according to claim 11, wherein the surface area is between about 0.1–5 m$^2$/g, and the average grain size is between about 4–8 μm.

13. In a tooth cleaning composition, the improvement comprising that the composition Contains hydroxyapatite as defined according to claim 11.

14. A process according to claim 1, wherein said molar ratio of Ca:P is between about 0.3:1 to 0.5:1.

15. A process according to claim 1, wherein said hydroxyapatite product contains substantially no dicalcium phosphate.

16. A process according to claim 1, wherein said hydroxyapatite product has a high crystallinity of a degree of crystallization of greater than about 95%.

* * * * *